US009336669B2

(12) United States Patent
Bowden et al.

(10) Patent No.: US 9,336,669 B2
(45) Date of Patent: May 10, 2016

(54) TAMPER EVIDENT POINT OF CONTAINMENT, INVENTORY AND ACCOUNTABILITY SYSTEM AND METHOD

(75) Inventors: Robert A. Bowden, Far Hills, NJ (US); Michelle Hossenlopp, Belton, TX (US)

(73) Assignee: The United States of America as represented by The Secretary of the Army, Washington, DC (US)

( * ) Notice: Subject to any disclaimer, the term of this patent is extended or adjusted under 35 U.S.C. 154(b) by 412 days.

(21) Appl. No.: 13/814,600

(22) PCT Filed: Aug. 8, 2011

(86) PCT No.: PCT/US2011/046982
§ 371 (c)(1),
(2), (4) Date: Apr. 11, 2013

(87) PCT Pub. No.: WO2012/019201
PCT Pub. Date: Feb. 9, 2012

(65) Prior Publication Data
US 2013/0194080 A1    Aug. 1, 2013

Related U.S. Application Data

(60) Provisional application No. 61/401,178, filed on Aug. 6, 2010.

(51) Int. Cl.
| | |
|---|---|
| *H04Q 5/22* | (2006.01) |
| *G08B 13/24* | (2006.01) |
| *B01L 3/00* | (2006.01) |
| *G01N 35/00* | (2006.01) |
| *B65D 85/00* | (2006.01) |
| *G01N 1/42* | (2006.01) |
| *G01N 1/00* | (2006.01) |

(52) U.S. Cl.
CPC ............ *G08B 13/2462* (2013.01); *B01L 3/545* (2013.01); *B65D 85/00* (2013.01); *G01N 35/00732* (2013.01); *B01L 2200/141* (2013.01); *B01L 2300/022* (2013.01); *G01N 1/42* (2013.01); *G01N 2001/007* (2013.01); *G01N 2035/00782* (2013.01)

(58) Field of Classification Search
CPC .......................... G07C 5/008; G01N 35/00732
USPC ........................................ 340/5.1, 572.8, 571
See application file for complete search history.

(56) References Cited

U.S. PATENT DOCUMENTS

| | | |
|---|---|---|
| 4,883,294 A | 11/1989 | Goodspeed |
| 5,012,941 A | 5/1991 | Abrams et al. |
| 5,133,470 A | 7/1992 | Abrams et al. |

(Continued)

*Primary Examiner* — Vernal Brown
(74) *Attorney, Agent, or Firm* — Cahn & Samuels, LLP (57) ABSTRACT

The system in at least one embodiment includes a tamper evident specimen sample locking device that in a further embodiment includes an embedded data storage mechanism. A method for using the system in at least one embodiment allows for efficiently and securely creating, maintaining, identifying, tracking, and controlling inventories (either prospective or retrospective) of biological and chemical sample containers and their contents, while eliminating potential loss and degradation associated with handling the samples. The system in at least one embodiment includes a sample container tray or cryogenic box having one or more integrated RFID readers within an associated smart lid that sense RFIDs associated with the individual samples thereby eliminating the need to remove, visually inspect, and/or handle the samples.

14 Claims, 7 Drawing Sheets

(56) References Cited

U.S. PATENT DOCUMENTS

| | | |
|---|---|---|
| 6,861,954 B2 | 3/2005 | Levin |
| 7,070,053 B1 | 7/2006 | Abrams et al. |
| 7,095,324 B2 | 8/2006 | Conwell et al. |
| 7,178,416 B2 | 2/2007 | Whelan et al. |
| 7,201,410 B1 | 4/2007 | Lassen |
| 7,216,592 B2 | 5/2007 | Krech et al. |
| 7,275,682 B2 | 10/2007 | Excoffier et al. |
| 7,286,055 B2 | 10/2007 | Girvin et al. |
| 7,293,715 B2 | 11/2007 | Bargach et al. |
| 7,350,689 B1 | 4/2008 | Campbell |
| 7,350,703 B2 | 4/2008 | Ambartsoumian |
| 7,377,447 B2 | 5/2008 | Oberle |
| 7,701,346 B2 | 4/2010 | Lindsay et al. |
| 7,703,687 B2 | 4/2010 | Barczyk et al. |
| 7,705,734 B2 | 4/2010 | Martinelli |
| 7,782,212 B2 * | 8/2010 | Burns et al. ............. 340/572.8 |
| 2001/0030192 A1 * | 10/2001 | Redmond ............. B65D 5/746 220/203.08 |
| 2003/0174046 A1 | 9/2003 | Abrams |
| 2006/0004524 A1 * | 1/2006 | Aucoin et al. ............. 702/19 |
| 2006/0117717 A1 * | 6/2006 | Canseco ............. 53/467 |
| 2007/0114140 A1 | 5/2007 | Portier |
| 2007/0145150 A1 | 6/2007 | Barczyk et al. |
| 2008/0117058 A1 | 5/2008 | Oberle |
| 2008/0121707 A1 | 5/2008 | Phillips et al. |
| 2009/0306620 A1 | 12/2009 | Thilly et al. |

* cited by examiner

TAMPER EVIDENT POINT OF CONTAINMENT, INVENTORY AND ACCOUNTABILITY SYSTEM AND METHOD

I. CROSS-REFERENCE TO RELATED APPLICATIONS

This application is the National Stage of International Application No. PCT/US2011/046982, filed on Aug. 8, 2011, which claimed the benefit of U.S. Provisional Patent Application Ser. No. 61/401,178 filed Aug. 6, 2010, which is incorporated herein by reference. The International Application No. PCT/DE2011/046982 was published on Feb. 2, 2012.

II. FIELD OF THE INVENTION

The present invention in at least one embodiment relates to a system and method for providing an indication of whether a specimen sample has been tampered with or otherwise accessed. The present invention in at least one embodiment relates to a system and method for identifying and tracking specimen samples currently in storage conditions within containers, as well as, prospectively collected specimen samples. More particularly, the present invention in at least one embodiment relates to a tamper evident RFID inventory and accountability system and method for efficiently identifying and tracking biological and chemical specimens while being stored.

III. BACKGROUND OF THE INVENTION

Biological and chemical sample containers are commonly used in the medical, chemical, bioscience and drug research and testing industries. These containers are typically made of plastic, glass, or a similar non-reactive material and cover a range of sizes and types. However, smaller vials such as, 0.5 mL, 1 mL, 1.5 mL, 1.8 mL, and the like, are widely used in the medical, chemical, bioscience and drug research and testing industries. In these industries, unique specimen samples (for example, blood or urine in the drug testing industry) are maintained in individual vials. The individual vials are often stored within a container such as a box that typically holds up to 100 vials per box. Laboratories and research facilities are two examples where the mission requires storage of specimen samples that number into the tens of thousands or hundreds of thousands in incubators, refrigerators, freezers, cryogens, and similar storage devices with increasing numbers of samples projected for collection, use and storage. In aggregate, these samples number into the millions. Therefore, given the number of samples that are stored it is imperative that each specimen sample is reliably identified and tracked in order to maintain the integrity of the research and testing, and to meet applicable reporting requirements.

Some prior specimen identification and tracking systems have including printed (written or handwritten) labels that require visual inspection, or a unique bar code along the side of the container that is typically located and scanned using a hand held optical scanner. The printed label systems require users to remove the trays from storage and remove the specimen vials from the tray in order to identify and track the specimen. The bar code labeling systems utilize a light beam emitted from the scanner to "read" the bar code label. Because the relationship of the single-use test device or biological or chemical sample container is by nature transitory and such items are either discarded following use or cleansed by some process, prior systems did not provide a mechanism for positive tracking of the sample or test object other than by barcode or handwritten labels. Handwritten, adhesive label and bar code technology requires positive line-of-sight and may be adversely affected by the contents of the sample, reagents and/or by physical handling of the test device or specimen container which may degrade the label such that it cannot be read by human eye or an optical reader. Bar code technology also requires sample containers to be removed from storage and handled individually, resulting in lengthy inventory processes that create a significant potential for loss or damage to the container and/or specimens because of their removal from the storage device.

Securely and efficiently protecting samples against tampering and contamination remains a critical concern. The vast majority of the existing samples are stored insecurely in a manner prone to tampering and contamination—often in vials having only a flip top, screw top, etc. that can be easily breached by unauthorized personnel. For example, a critical and urgent need exists to maintain a one-hundred percent inventory and accountability of all Biological and Select Agent and Toxin (BSAT) samples in the Department of Defense (DoD) Inventory. In addition, mechanisms must be put in place to monitor and notify of tampering or unauthorized access to such samples. BSAT samples must be secured in a manner appropriate to guard against misuse, theft, loss or accidental release. These inventory and security measures must be implemented in a coordinated manner that balances security and efficiency with access to scientists for the legitimate use of BSAT. The same need applies to numerous biological science laboratories in hospitals, blood storage facilities, fertility clinics, etc., i.e., anywhere inventory and accountability of valued or sensitive items are required at a moment's notice.

Increasing regulatory requirements by human and animal ethical use policies, as well as, state agency imposed requirements mandate accurate and efficient accountability of all specimens, prospective and retrospective. The increased requirements in addition to the mounting volumes of samples requiring storage demands a significant amount of additional administrative work to efficiently, securely and accurately inventory and account for biological samples. Currently, most laboratory personnel simply write a coded sequence number on the sample container directly or use an adhesive label to identify the contents. Limited by line-of-sight, the primary strategy to account for a sample is to physically remove it from its current storage condition such as in an incubator at approximately 37 C or a freezer, count the vials one-by-one, affirming that the label indicates a material exists in the container. Multiple permutations on line-of-sight strategies to streamline the inventory process are used. However, additional limitations create significant inefficiencies. But these inefficiencies can be overcome by use of the present invention.

IV. SUMMARY OF THE INVENTION

In at least one embodiment, the present invention provides a tamper evident sample locking device, including an elongated locking strip having two ends that are foldable to mate with each other, wherein the elongated locking strip is made of a resilient material that provides a physical indication of tampering and includes an opening capable of receiving and securely engaging the exterior surface of a specimen sample container, wherein the opening is proximate the middle of the elongated locking strip; locking mechanisms substantially proximate both ends of the elongated locking strip, wherein the locking mechanisms fittingly engage with and lock to each other when the ends of the elongated locking strip are folded to mate with each other; wherein the specimen sample container is securely locked within the elongated locking strip such that removal of the specimen sample container provides a physical indication of tampering on the elongated locking strip. In a further embodiment, the device includes a data storage device in the locking strip.

In at least another embodiment, the present invention provides a tamper evident sample locking device, including a central hub, wherein the central hub is capable of engaging an end of a specimen sample container; multiple elongated locking members attached to the central hub, wherein the multiple elongated locking members are capable of engaging the exterior surface of the specimen sample container and include multiple locking structures longitudinally spaced along the length of the locking members; and a locking collar having multiple locking apertures, wherein the locking apertures are capable of receiving and securely engaging the exterior surface of a specimen sample container, and receiving and locking the multiple locking structures of the multiple elongated locking members; wherein the specimen sample container is securely locked within the elongated locking strip such that removal of the specimen sample container provides a physical indication of tampering on the elongated locking strip. In a further embodiment, the device includes a data storage device in the hub.

In at least another embodiment, the present invention provides a method including writing information related to an individual sample to an RFID device, wherein the RFID device is uniquely associated with the sample; placing the individual sample in a specimen container device, wherein the specimen sample device is attached to the RFID device; writing any updated information to the RFID device; storing the specimen sample container, wherein the specimen sample container is stored within an environment that maintains the integrity of the specimen sample; and inventorying the specimen sample container by interrogating the RFID associated with the specimen sample container.

In at least another embodiment, the present invention provides a method for maintaining, tracking, and identifying the integrity of a specimen sample, the method including writing information related to a stored specimen sample to an RFID device, wherein the RFID device is associated with the sample; removing the specimen sample from storage; placing and locking the RFID device on a specimen sample container enclosing the specimen sample; returning the specimen sample container to storage, wherein the specimen sample container is stored within an environment that maintains the integrity of the specimen sample; and inventorying the specimen sample container by interrogating the RFID associated with the specimen sample container.

In at least a further embodiment, the present invention provides tamper evident sample locking device including an elongated locking strip having two ends that are foldable to mate with each other, wherein the elongated locking strip is made of a resilient material that provides a physical indication of tampering and includes an opening capable of receiving and securely engaging the exterior surface of a specimen sample container; locking mechanisms disposed on the elongated locking strip, wherein the locking mechanisms fittingly engage with and lock to each other when the ends of the elongated locking strip are folded to mate with each other; wherein the specimen sample container is securely locked within the elongated locking strip such that removal of the specimen sample container provides a physical indication of tampering on the elongated locking strip.

In at least a further embodiment, the present invention provides a tamper evident sample locking device including an elongated locking strip having two ends that are foldable to mate with each other, wherein the elongated locking strip is made of a resilient material that provides a physical indication of tampering and includes means for receiving and securely engaging an exterior surface of a specimen sample container, wherein the means is proximate the middle of the elongated locking strip; locking mechanisms substantially proximate both ends of the elongated locking strip, wherein the locking mechanisms fittingly engage with and lock to each other when the ends of the elongated locking strip are folded to mate with each other, and wherein the locking mechanisms include openings and raised projections, wherein each of the projections engage with and lock to at least one of openings; an RFID device connected to the elongated locking strip, wherein the elongated locking strip further includes at least one depression and the RIFD device is disposed within one or more of the at least one depression; and at least one fault line, wherein the at least one fault line allows the elongated fastening strip to fold more easily.

In at least a further embodiment, the present invention provides a tamper evident sample locking device including an elongated locking strip having two ends that are foldable to mate with each other, wherein the elongated locking strip is made of a resilient material that provides a physical indication of tampering and includes means for receiving and securely engaging an exterior surface of a specimen sample container, wherein the means is proximate the middle of the elongated locking strip; locking apertures substantially proximate both ends of the elongated locking strip, wherein the locking apertures align such that a locking mechanism is capable of engaging the aligned locking apertures; and a locking mechanism that fittingly engages with and locks to the locking apertures such that both ends of the elongated locking strip are securely fastened to each other.

In at least a further embodiment, the present invention provides a system including a locking collar means; and a container cap securing means; wherein the locking collar means is capable of engaging the container cap securing means in a manner that securely locks a container within the container cap securing means such that the container cannot be removed without providing a physical indication of tampering.

Given the following enabling description of the drawings, the apparatus should become evident to a person of ordinary skill in the art.

VI. DETAILED DESCRIPTION OF THE DRAWINGS

While the present invention is susceptible of embodiments in various forms, there is shown in the drawings and will hereinafter be described some exemplary and non-limiting embodiments, with the understanding that the present disclosure is to be considered an exemplification of the invention and is not intended to limit the invention to the specific embodiments illustrated.

The present invention provides different embodiments for devices, methods and systems for creating, maintaining, identifying, tracking, and controlling inventories of biological and chemical samples containers and their contents at the point of containment. In at least some embodiments, the present invention provides a tamper evident system and method that is capable of use in a retrofit implementation, while in further embodiments portions of the system are incorporated into the construction of the sample container. In at least some embodiments, the present invention provides a tamper evident RFID inventory tracking and accountability system and method. In at least some embodiments, the present invention provides a sample lock that includes an embedded storage medium, such as an RFID chip, integrated circuit (IC), or comparable technology, that allows the sample to be quickly and easily identified, tracked and accounted for without the need to remove, visually inspect, and/or handle the sample. In at least some embodiments, the present invention provides a sample container tray or box having one or more integrated RFID transceivers that interrogate and report the RFIDs associated with the individual samples.

Figure 1:
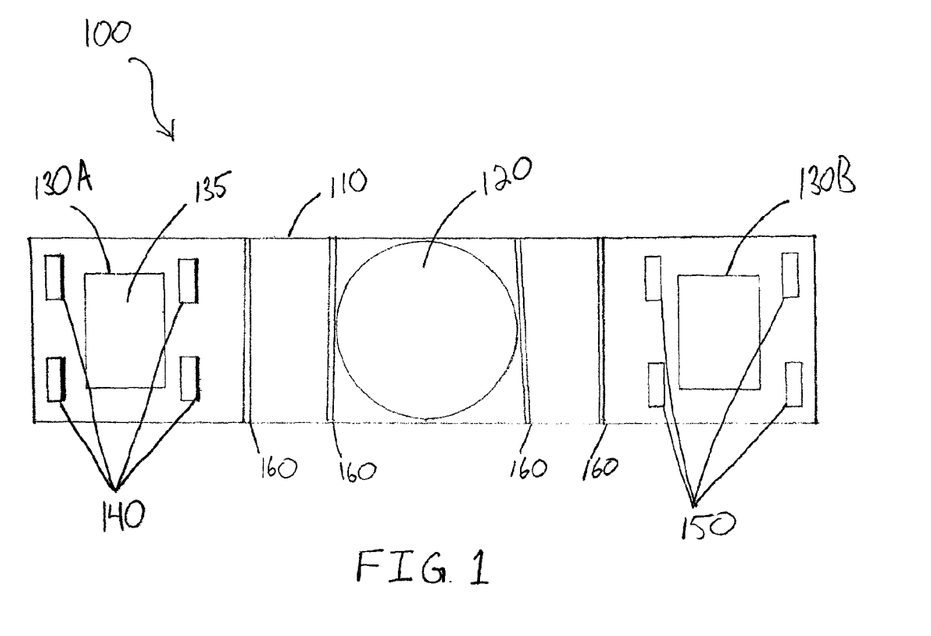
FIG. 1 illustrates an example of a tamper evident sample locking device in accordance with an embodiment of the present invention.

In at least one embodiment, the present invention provides a tamper evident sample locking device, as illustrated in FIG. 1. The sample locking device 100 includes a locking strip 110 having an opening (or locking collar) 120 that is sized and designed to fit over the top (or bottom) of a specimen sample container 170 and fittingly engage the sidewall or cap 175 of the container 170 such that the ends of the locking device 100 can be folded to engage each other and fasten into a locked position. In at least one embodiment, the opening 120 is substantially centered on the locking strip 110. Based on this disclosure, it should be understood that cap 175 and container 170 can be a variety of combinations that are used for storing samples. The locking strip 110 is preferably made of a resilient material, e.g., polypropylene, resin, or a similar substantially rigid polymer. The material should provide a clear indication of tampering in the event of being broken, stretched, cut, torn, burned, and the like. The locking strip 110 may include one or more depressions 130A, 130B that are sized and designed to receive and secure an optional embedded data storage mechanism 135, e.g., an RFID chip, integrated circuit, transceiver, or similar technology that is capable of receiving and storing data, as well as transmitting data when queried. The optional embedded data storage mechanism 135 may be affixed permanently or semi-permanently either during the manufacturing process or prior to deploying the sample locking device 100. In embodiments wherein the data storage mechanism 135 is an RFID chip, the RFID includes an integrated circuit (IC) and an antenna. The IC stores and processes information, modulates and demodulates radio frequency (RF) signals, and performs other specialized or programmable functions. The antenna receives and transmits RF signals. The RFID chip may be passive, active or battery assisted passive (BAP). A battery is included in active and BAP embodiments. The RFID chip may be designed so that the antenna, chip, battery, and/or wiring break when the RFID chip is tampered with. The RFID chip may thereby provide an indication of tampering, because of its inoperability.

The embedded data storage mechanism 135 can be programmed to store and transmit a variety of information related to the sample to an associated data reader (not shown), e.g., an RFID reader or transceiver. The embedded data storage mechanism 135 may also be designed to provide an electronic indication of tampering upon the opening of the locking device 100. The locking strip 110 includes locking mechanisms 140, e.g., raised notches having projections, which securely engage with apertures 150 to lock the sample locking device 100 around the cap 175 of a specimen sample container 170. Based on this disclosure, it should be appreciated that locking mechanisms can take a variety of structures. The locking strip 110 may also include optional depression or fault lines 160 that improve the deployment of the sample locking device 100 by making it easier to bend and lock the locking strip 110 around the sample container. Damage or removal of the sample locking device 100 will result in a traceable and/or noticeable alteration of the device 100. Once locked, the sample locking device 100 ensures that the sample container remains closed and cannot be opened without presenting a clear physical and/or electronic indication of tampering.

Figure 2:
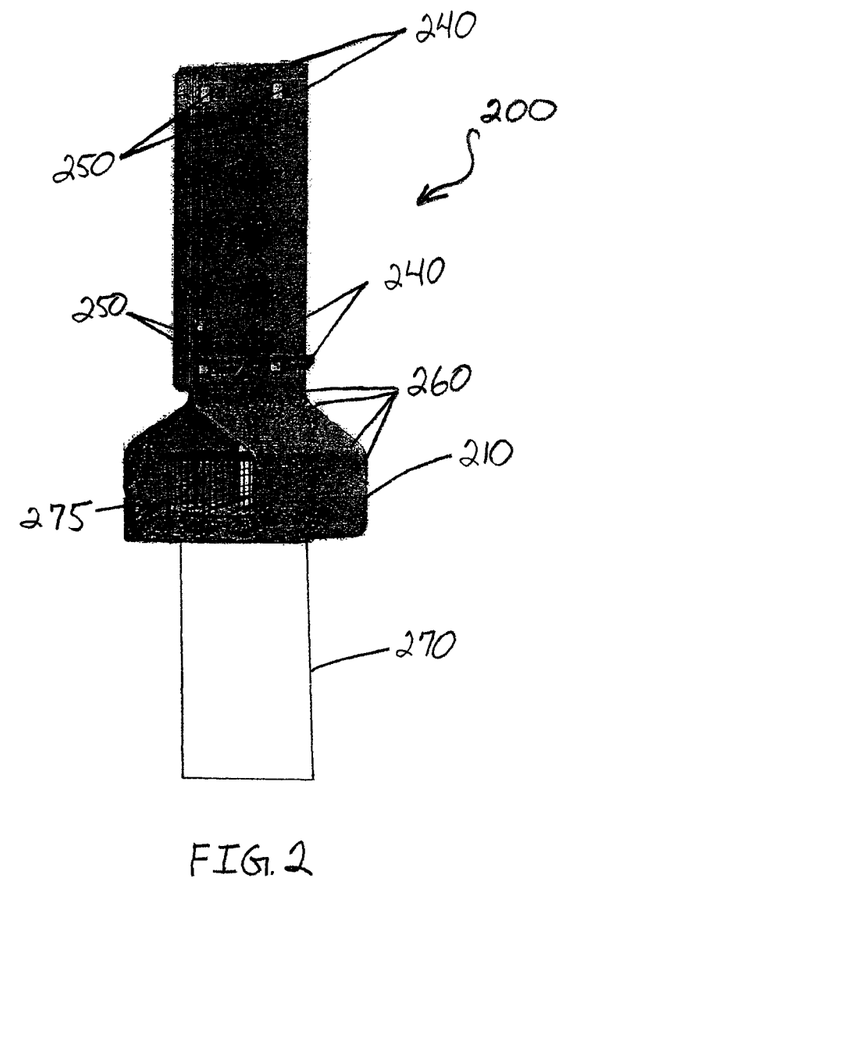
FIG. 2 illustrates an example of a tamper evident sample locking device in accordance with an embodiment of the present invention as illustrated in FIG. 1 in use.

As illustrated in FIG. 2, the sample locking device 200 is placed over the top or bottom of a specimen sample container 270 by inserting the sample container into opening (or locking collar) 220. The locking device 200 is then slid along the wall of the specimen sample container 270 until the locking device 200 fittingly and securely engages the specimen sample container 270. The ends of the locking strip 210 are then folded snugly over the end (top or cap) of the specimen sample container 270, e.g., along optional depression or fault lines 260, until the ends meet. The locking strip 210 may be provided with one or more depressions (not shown) that allow the locking strip 210 to fit around and securely enclose the embedded data storage mechanism 235. The locking mechanisms 240 are then inserted into the apertures 250 until the ends of the locking strip 210 securely abut each other and the locking mechanisms are securely and permanently engaged. Once locked around a specimen sample container 270, the sample locking device 200 can only be removed by breaking, stretching, cutting, tearing, burning, and/or otherwise destroying one or more of the components of the sample locking device 200 and thereby restricts access to the interior of the specimen sample container 270. Upon the opening of or attempted opening of the specimen sample container 270, the sample locking device 200 will be destroyed and/or provide clear physical evidence of tampering. The locking device in at least one further embodiment also provides an electronic indication of tampering via the embedded data mechanism. The length of the locking strips 210 can be a variety of lengths as long as the opposing ends of the locking strip 210 can engage each other. The sample locking device 200 thereby ensures that the sample container cap 275 remains closed and cannot be opened without presenting a clear physical and/or electronic indication of tampering.

Figure 3:
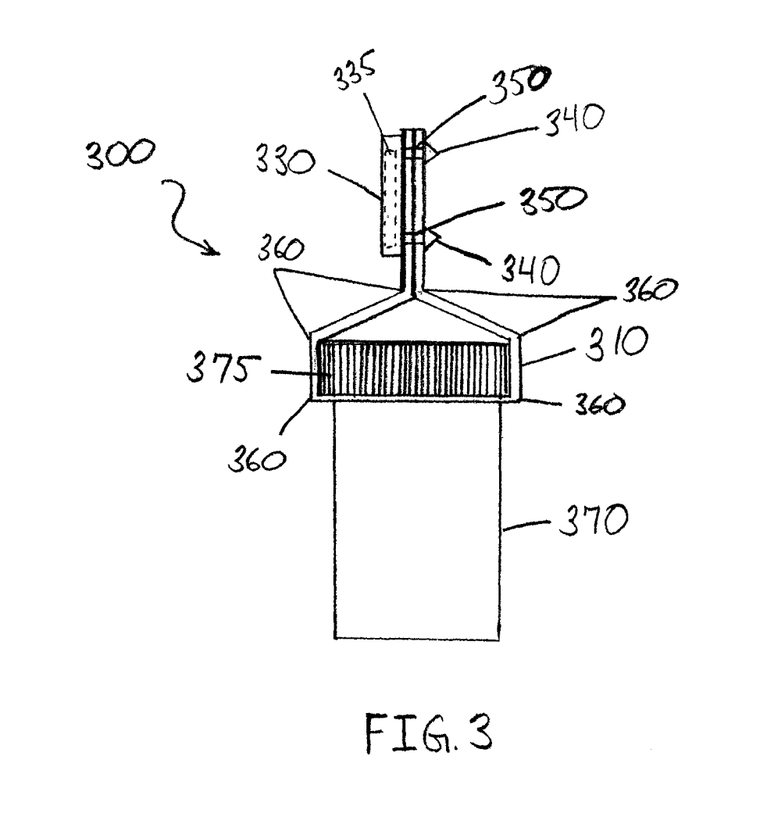
FIG. 3 illustrates an example of an alternative embodiment of a tamper evident sample locking device in accordance with an embodiment of the present invention.

FIG. 3 illustrates another alternative embodiment of a tamper evident sample locking device of the present invention. The sample locking device 300 provides similar functionality and operability as the device illustrated above with respect to FIGS. 1 and 2. However, the locking element 330 is embodied in a separate part that includes an optional embedded data mechanism 335 and locking mechanisms 340. The sample locking device includes a locking strip 310 having an opening (or locking collar) (not shown) that is sized and designed to fit over the top (or bottom) of a specimen sample container 370 and fittingly engage the sidewall or cap 375 of the container 370 such that the end of the locking device 300 can be folded to engage each other and fasten into a locked position. The locking strip 310 is preferably made of a resilient material, e.g., polypropylene, resin, or a similar substantially rigid polymer. The material should provide a clear indication of tampering in the event of being broken, stretched, cut, torn, burned, and the like. The locking strip 310 may include one or more locking apertures 350 that are sized and designed to receive and secure locking mechanisms 340. The locking mechanisms 340 include a structure, e.g., a projection, conical element, ball-like element, or the like, that passes through the locking apertures 350 and fittingly secures the ends of the locking strip 310 together. The locking mechanism 340 may also include an embedded data mechanism 335. The embedded data mechanism 335 may be placed within one or more option depressions (not shown) within the locking mechanism 340. The embedded data mechanism 335 may also be molded within the locking mechanism 335. The locking strip 310 thereby securely locks the sample locking device 300 around the cap 375 of a sample container 370. Based on this disclosure, it should be appreciated that locking mechanisms can take a variety of structures. The locking strip 310 may also include optional depression or fault lines 360 that improve the deployment of the sample locking device 300 by making it easier to bend and lock the locking strip 310 around the sample container. Damage or removal of the sample locking device 300 will result in a traceable and/or noticeable alteration of the device 300. Once locked, the sample locking device 300 ensures that the sample container remains closed and cannot be opened without presenting a clear physical and/or electronic indication of tampering.

Figure 4A:
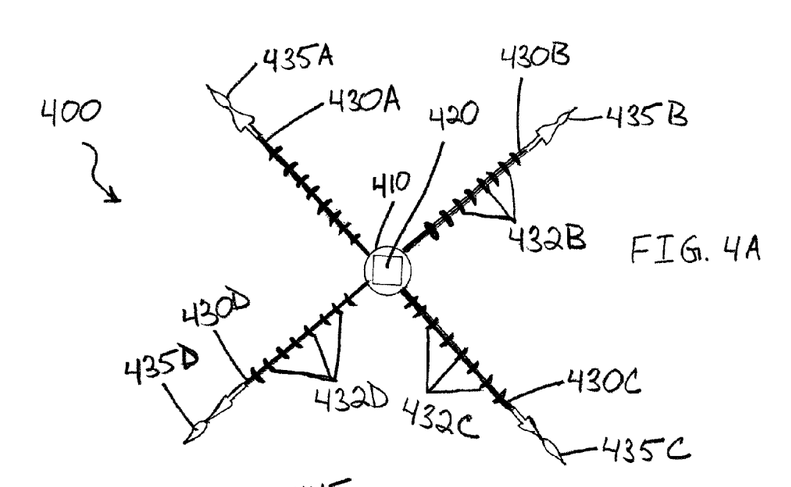
FIG. 4A illustrates an example of an alternative embodiment of a tamper evident sample locking device in accordance with an embodiment of the present invention.

FIGS. 4A-4D illustrate an alternative embodiment of a tamper evident sample locking device of the present invention. FIG. 4A illustrates a sample locking device 400 having a central hub 410 connected to multiple legs or lock members 430A, 430B, 430C, 430D. The hub 410 in a further alternative embodiment includes an optional embedded data storage mechanism 420. Locking members 430A, 430B, 430C, 430D are elongated and include multiple locking structures 432A, 432B, 432C, 432D, respectively. The locking members 430A, 430B, 430C, 430D may also, respectively, include tips 435A, 435B, 435C, 435D that are sized and designed to improve deployment. The locking structures of locking members 430A, 430B, 430C, 430D are sized and designed to pass through and lock within the locking apertures 445 of locking collar 440, illustrated in FIG. 4B. The locking apertures 445 are sized and designed to allow the raised structures 432A, 432B, 432C, 432D to pass through and be locked within the locking apertures 445. The locking structures 432A, 432B, 432C, 432D may include, for example, but are not limited to: ball-like structures, barbs, teeth, arrowheads or conical shaped members, concave and flat structures, conical structures, and the like that pass only one-way through the locking apertures 445. For example, the locking apertures may embody inverted cone-like structures that allow the raised structures 432A, 432B, 432C, 432D to pass through cone-like structure via the wide end of the cone such that the locking structures 432A, 432B, 432C, 432D are locked in position once they pass through small end of the cone.

The sample locking device 400 and locking collar 440 are preferably formed of a resilient but pliable material, e.g., polypropylene, resin, or a similar pliable rigid polymer. The material should be resilient enough in the data storage alternative embodiments to protect the optional embedded data storage mechanism, but pliable enough to allow the locking members to bend such that they can be drawn to fit snugly around the sample container 470 having a cap 275, as illustrated in FIG. 4D. The material should provide a clear indication of tampering in the event of being broken, stretched, cut, torn, burned, and the like. The locking collar 440 is also sized and designed to fittingly and securely engage the sample container 470 having cap 475 as illustrated in FIG. 4D. The locking collar 440 should be pliable enough to flex or stretch around the sample container 470 but should have enough tension be secure around the sample container 470. The locking collar 440 may embody a variety of arrangements including high tensile bands, accordion-like rings, crisscrossed rings, and the like. In some embodiments, the locking collar 440 is formed with the locking members 430A, 430B, 430C, 430D. In other embodiments, the locking collar 440 is attached to or incorporated into the specimen container 470. In further embodiments, the central hub 420 is attached to the sample container cap 475.

As illustrated in FIG. 4D, the sample locking device is deployed by sliding the locking collar 440 from one end (such as the bottom) and along the wall of the sample container 470 until the locking collar 440 fittingly and securely engages the sample container 470. In an alternative embodiment, the locking collar 440 is wrapped around the sample container 470. The central hub 410 is then placed over the cap 475 (or bottom) of the sample container 470. The locking members 430 are then bent along the wall of the sample container 470 and passed through the locking apertures 445. The central hub 410 (and embedded data storage medium) is secured over the cap 475 of the sample container 470 and the locking members 430 are tightened within the locking collar 440 until the sample locking device 400 is fittingly and securely engaged with the sample container 470. Once locked, the sample locking device 400 can only be removed by breaking, stretching, cutting, tearing, burning, and/or otherwise destroying one or more of the components of the sample locking device 400. The sample locking device 400 thereby ensures that the sample container cap 475 remains closed and cannot be opened without presenting a clear physical and/or electronic indication of tampering depending on the embodiment.

In further alternative embodiments, the locking collar as discussed above with respect to FIGS. 1-4D may include a plurality of teeth that extend from the locking collar to help secure the locking collar onto the specimen sample container. For example, the teeth may extend from the locking collar in a direction that is substantially longitudinal and inward with respect to the specimen sample container such that the teeth abut the specimen sample container. The teeth allow the locking collar to only be moved in one direction, i.e., onto the specimen sample container, such that when the locking collar is in the "locked" position attempts to remove, reverse, or back off the locking collar the teeth "bite" into the specimen sample container and prevent the locking collar from being removed.

While the preferred embodiments of the above-described invention include an embedded data storage mechanism, the invention is capable of being deployed without the use of such a mechanism. In embodiments that do not include a data storage mechanism, the sample locking device when placed over the cap would still prevent access to the sample container and provide a clear physical indication of tampering. Those embodiments would therefore still function as an effective tamper evident sample locking device. However, those embodiments would not provide an electronic indication of tampering.

Figure 5:
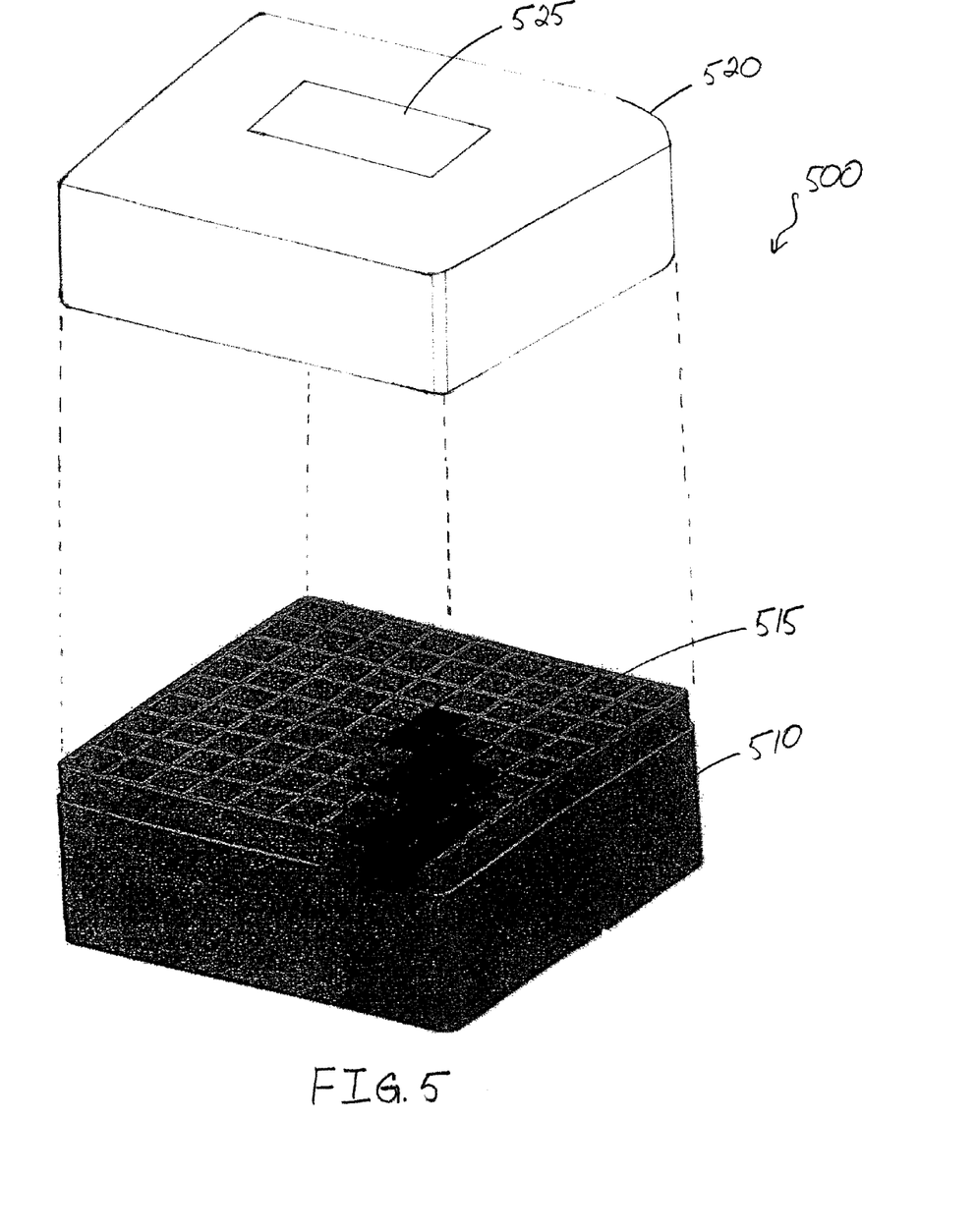
FIG. 5 illustrates an example of an embodiment of a smart sample container tray and lid in accordance an embodiment of the present invention.

FIG. 5 illustrates another aspect of the tamper evident sample locking device of the present invention. A smart sample container tray such as a cryogenic box 500 includes a bottom tray 510 and smart lid 520. The bottom tray 510 includes an array of sample container holders 515 that may be sized and designed to hold a variety of standard sample container holders. For example, the cryogenic box may be of a standard size, e.g., 4.875 inches×4.875 inches×1.3125 inches, or 5.2 inches×5.25 inches×2 inches, or 3 inches×3 inches×2 inches. The array of sample container holders 515 may be arranged, e.g., 9 by 9 or 10 by 10, in order to securely hold a standard number of sample containers, e.g., 81 or 100. The smart lid 520 is sized and designed to engage with the cryogenic box 510 in a cooperating fashion such that the sample containers are securely held within the array of sample container holders 515 inside the cryogenic box 510. The smart lid 520 includes one or more embedded transceivers 525, e.g., an RFID reader, which is capable of receiving and transmitting data. The one or more embedded transceivers 525 should be tuned and arranged to communicate with all of the desired samples stored within the cryogenic box 500. The embedded transceiver 525 may be programmed to transmit data according to a schedule or upon being queried or instructed by an associated computer (not shown) to initiate interrogation and receive reporting signals from the associated embedded transceiver 525. The embedded transceiver 525 may communicate with an associated computer on a variety of known wireless and/or wired communication platforms (e.g., wire harness or bus) and protocols, as appropriate. The placement of the embedded transceiver 525 therefore allows samples to be stored, maintained, identified, tracked, and reported without having to remove the samples from storage, handle the samples, visually inspect the samples, etc. Further, given the vast number of samples that are often stored and the heightened tracking and reporting requirements, at least one tracking embodiment significantly improves the integrity, efficiency and accuracy of the storing, maintaining, identifying, tracking, and reporting requirements.

The cryogenic box 500 in at least one embodiment is formed of a suitable resilient and temperature resistant material that is appropriate for the intended use of the cryogenic box 500. The materials should be appropriate to withstand very low temperatures (for example, temperatures associated with use in liquid nitrogen) and/or very high temperatures (for example, temperatures associated with use in incubators) and the like without presenting a risk of deterioration to the samples contained within the cryogenic box 500 or the cryogenic box 500 itself. The cryogenic box 500 is therefore suitable for use within a variety of storage and testing environments including storage freezers, refrigerators, incubators, etc.

In some embodiments, the smart sample box or cryogenic box may not include a smart lid. While the embedded transceiver 525 is illustrated as being contained with the smart lid 520, other arrangements of the embedded transceiver 525 may also be utilized without departing from the invention, including placing the embedded transceiver within the bottom tray 510, beneath the bottom tray 510, above the top 520, or within very close proximity to the samples such that the communication can be established. In other embodiments, the embedded transceiver 525 may be attached to or embedded in a mat suitable for use within the storage environment such as within a refrigerator or cryogenic freezer. The mat can then be placed within the storage device, e.g., on the shelf of a refrigerator, such that the embedded transceiver 525 can sense signals from within storage trays placed on the shelf.

Figure 6:
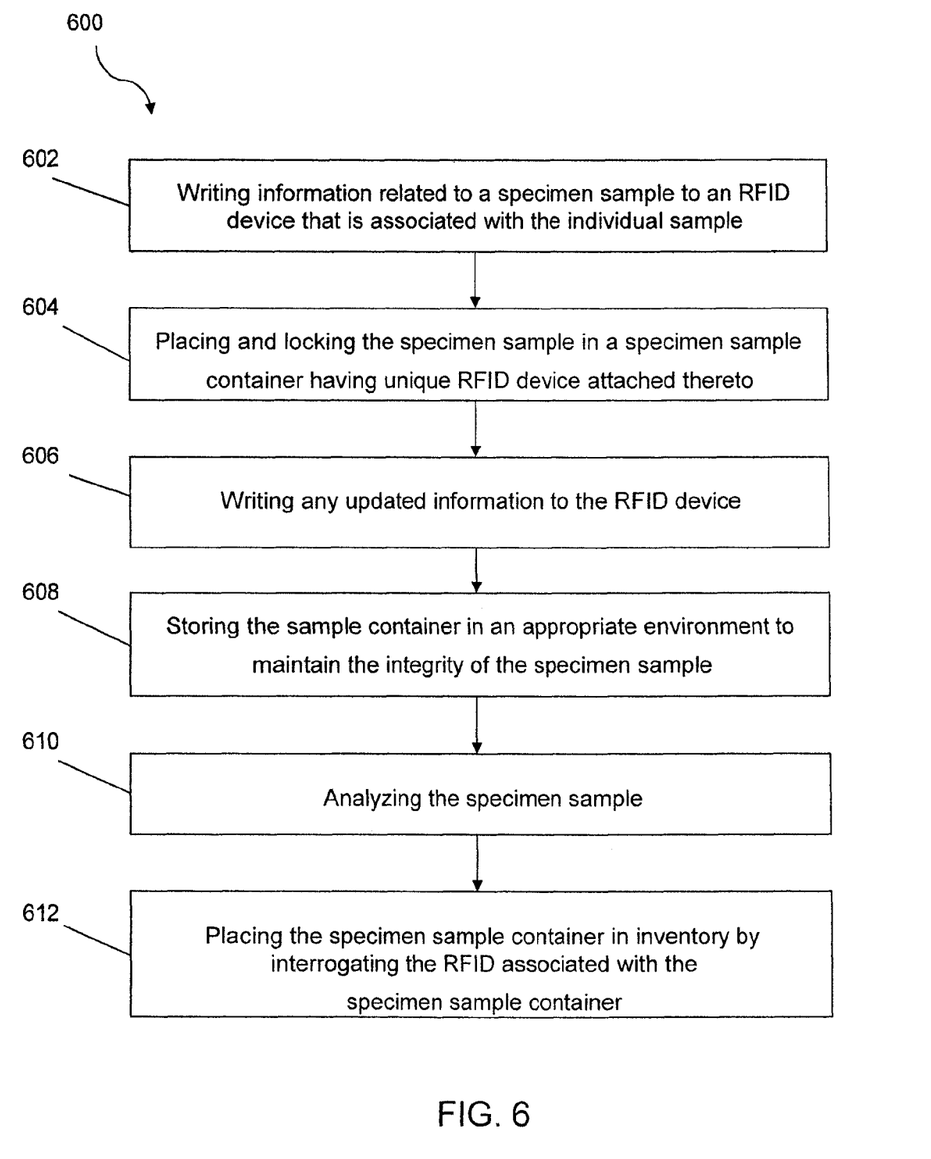
FIG. 6 illustrates a method of maintaining, tracking and identifying the integrity of a specimen in accordance with an embodiment of the present invention.

FIG. 6 illustrates a method of maintaining, tracking and identifying the integrity of a specimen sample in accordance with the present invention. The method 600 begins at 602 by writing information related to the sample to an RFID device that is uniquely associated with the individual sample, i.e., a data device that is attached to the sample container. The information may include, for example, the date, a unique identification of the sample container (vial), text, research data, etc. At 604, placing and locking the specimen sample in the specimen sample container having the RFID device attached thereto. At 606, writing any updated information to the RFID device. This updated information may include, for example, the date, time, sample lot size, etc. At 608, storing the sample container in an appropriate environment to maintain the integrity of the specimen sample. At 610, sending the specimen sample container to a laboratory for analysis. At 612, inventorying the specimen sample container by interrogating the RFID associated with the specimen sample container.

The method of present invention provides a reliable and accurate specimen sample maintenance, tracking and identifying method that ensures the integrity of the specimen samples during storage, testing and/or transport. The method utilizes an embedded data storage mechanism that is capable of receiving and storing data, as well as transmitting data when queried. The RFID provides a means of continual and instant querying and verification of the specimen sample. In addition to specimen vials other suitable container may also be used including, for example, Petri dishes, flasks, bottles, test-tubes, re-sealable plastic bags, pharmaceutical type storage containers, bins, clam-shell cases, bottle stoppers or corks and plastic cassettes.

Figure 7:
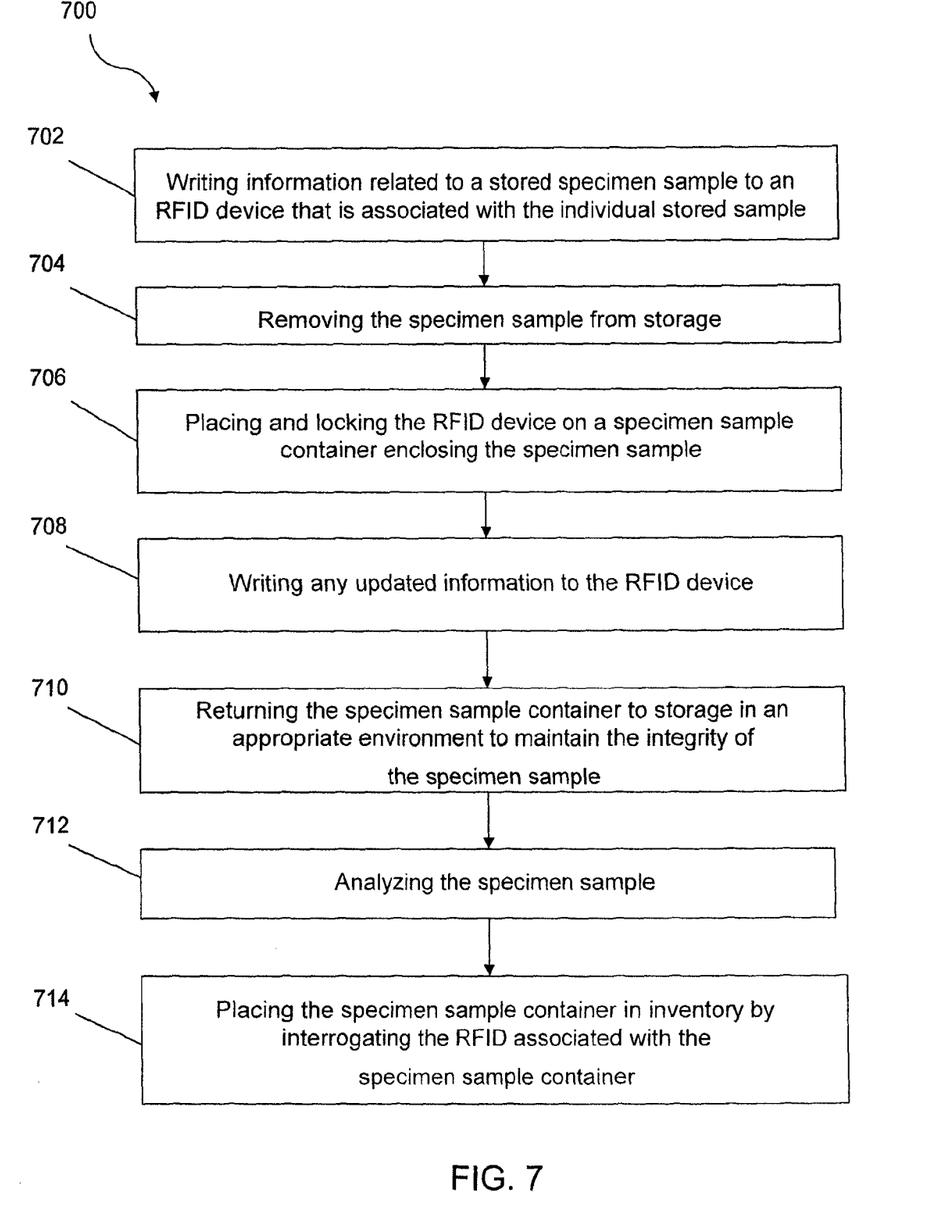
FIG. 7 illustrates an alternative method of maintaining, tracking and identifying the integrity of a specimen in accordance with an embodiment of the present invention.

FIG. 7 illustrates an alternative method of maintaining, tracking and identifying the integrity of a specimen sample in accordance with the present invention. The method 700 is suitable for "retro-fitting" a stored sample with an RFID device of the present invention. The method 700 begins at 702 by writing information related to a stored specimen sample to an RFID device, i.e., a specimen sample locking device having an embedded data storage device. The information may include, for example, the date, a unique identification of the sample container (vial), text, research data, etc. At 704, removing the specimen sample from storage. At 706, placing and locking the specimen sample in the specimen sample container within the RFID specimen sample locking device. At 708, writing any updated information to the RFID device. This updated information may include, for example, the date, time, sample lot size, etc. At 710, returning the specimen sample container to storage in an appropriate environment to maintain the integrity of the specimen sample. At 712, analyzing the specimen sample, wherein the analysis may require sending the specimen sample container to a laboratory. At 714, inventorying the specimen sample container by interrogating the RFID associated with the specimen sample container.

An alternative embodiment includes using the above-described embodiments to secure sample containers. An existing sample container is removed from storage, for example, as part of an inventory. Over the container is slid the collar of one of the above-described locking devices. The collar engages and/or tightens around the container to resist removal. The locking components are attached or folded over the cap of the sample container securing the cap to the sample container such that if the sample container is accessed, the locking device will need to be physically manipulated and/or damaged resulting in a physical indication that access of the sample container has occurred. One particularly useful application of this method is in situations where a chain of custody is desired.

Figure 4B:
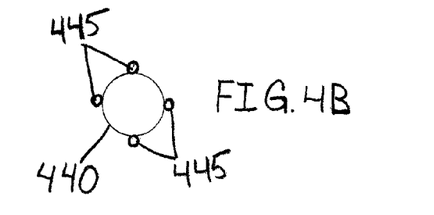
FIG. 4B illustrates an example a locking collar of the alternative embodiment of the tamper evident sample locking device as illustrated in FIG. 4A.
Figure 4C:
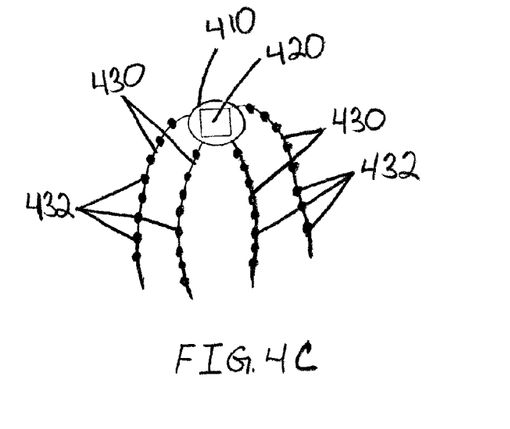
FIG. 4C illustrates another view of the tamper evident sample locking device in accordance with an embodiment of the present invention as illustrated in FIG. 4A.
Figure 4D:
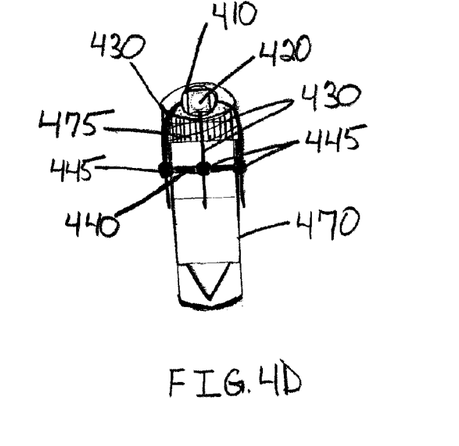
FIG. 4D illustrates an example of the tamper evident sample locking device in accordance with an embodiment of the present invention as illustrated in FIG. 4A, in use.

In a further alternative embodiment, the embodiment depicted in FIGS. 4A-4C is used as described in the previous paragraph; however, when access of the sample container is desired, the hub 410 is physically removed by, for example, cutting the locking members 430A, 430B, 430C, 430D. After the researcher or other user is finished, they attach a new hub 410 to the previously used collar. In an embodiment where the hub 410 includes a data storage mechanism, the data from the previous data storage mechanism is transferred to the new data storage mechanism along with the annotation of access to the sample container.

The present invention in at least one embodiment can be added, i.e., retrofitted, to existing sample containers to provide an efficient and effective means for the identification, inventory, tracking and reporting of the samples. The ability to retrofit previously existing inventories with tamper-evident RFID locking devices provides significant savings of time and resources related to the maintenance, inventory and reporting processes.

The present invention in a further embodiment utilizes an RFID transceiver and system which can actively or passively query on-demand or as programmed to report all or part of the data associated with the RFID embedded containers. The RFID chip is imprinted with identification that can allow or disallow access to the stored data contingent on the user-query and validation response. The system in at least one embodiment reads from outside a storage container the presence of the RFID embedded sample containers. The system in a further embodiment is programmed to report an alert signal upon the detection of tampering of a sample container.

The embedded data storage device of the present invention may also be used to provide electronic data generated entries that auto-fill an associated electronic laboratory notebook, inventory record, inspection report or similar documentation. The embedded data storage device of the present invention may also communicate with and report the detection of other devices including, for example, stir bars, incubators, etc., to report start/stop time of incubation, stirring, experiment condition or designated experimental endpoint.

The exemplary embodiments described above may be combined in a variety of ways with each other. Furthermore, the steps and number of the various steps illustrated in the figures may be adjusted from that shown. It should be noted that the present invention may, however, be embodied in many different forms and should not be construed as limited to the embodiments set forth herein; rather, the embodiments set forth herein are provided so that the disclosure will be thorough and complete, and will fully convey the scope of the invention to those skilled in the art. The accompanying drawings illustrate exemplary embodiments of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. For example, collar means for receiving and securely engaging an exterior surface of a specimen sample container include any of the above-described locking collars. An example of cap securing means for securing a cap to a specimen sample bottle includes any of the above-described locking members and/or hubs. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the embodiments described above can be configured without departing from the scope and spirit of the invention. Therefore, it is to be understood that, within the scope of the appended claims, the invention may be practiced other than as specifically described herein.

We claim:

1. A tamper evident sample locking device comprising:
a central hub, wherein said central hub is capable of abutting an end of a specimen sample container;
multiple elongated locking members attached to said central hub, wherein said multiple elongated locking members are capable of engaging the exterior surface of the specimen sample container and each includes a plurality of locking structures longitudinally spaced along the length of said locking members; and
a locking collar having multiple locking apertures, wherein said locking collar is capable of receiving and securely engaging an exterior surface of the specimen sample container, and wherein said locking apertures are capable of receiving and locking said multiple locking structures of said multiple elongated locking members.

2. The tamper evident sample locking device according to claim 1, further comprising an embedded data storage mechanism attached to said central hub.

3. The tamper evident sample locking device according to claim 2, wherein said embedded data storage mechanism provides an electronic indication of tampering upon the removal of the sample container.

4. The tamper evident sample locking device according to claim 1, wherein said specimen sample container is securely locked within said elongated locking members such that removal of the specimen sample container provides a physical indication of tampering on at least one of said elongated locking members.

5. The tamper evident sample locking device according to claim 1, wherein said central hub, said elongated locking members, and said locking collar are formed of a resilient material.

6. The tamper evident sample locking device according to claim 5, wherein at least one of said central hub, said elongated locking members, and said locking collar provides a physical indication of tampering upon the removal of the specimen sample container.

7. The tamper evident sample locking device according to claim 1, wherein said multiple locking structures are selected from the group comprising ball-like structures, barbs, teeth, arrowheads or conical shaped members, concave and flat structures, conical structures.

8. The tamper evident sample locking device according to claim 1, wherein each of said multiple elongated locking members includes at least one pointed tip.

9. The tamper evident sample locking device according to claim 2, wherein said locking collar engages the exterior surface of the specimen sample container at a point spaced from a second end of the specimen sample container.

10. The tamper evident sample locking device according to claim 2, wherein said specimen sample container is securely locked within said elongated locking members such that removal of the specimen sample container provides a physical indication of tampering on at least one of said elongated locking members.

11. The tamper evident sample locking device according to claim 2, wherein said central hub, said elongated locking members, and said locking collar are formed of a resilient material.

12. The tamper evident sample locking device according to claim 11, wherein at least one of said central hub, said elongated locking members, and said locking collar provides a physical indication of tampering upon the removal of the specimen sample container.

13. The tamper evident sample locking device according to claim 2, wherein said multiple locking structures are selected from the group comprising ball-like structures, barbs, teeth, arrowheads or conical shaped members, concave and flat structures, conical structures.

14. The tamper evident sample locking device according to claim 2, wherein each of said multiple elongated locking members includes at least one pointed tip.

* * * * *